(12) United States Patent
Bürger et al.

(10) Patent No.: US 10,018,604 B2
(45) Date of Patent: Jul. 10, 2018

(54) CONNECTOR UNIT AND CONNECTING SYSTEM FOR CONNECTING CAPILLARIES, IN PARTICULAR FOR HIGH-PERFORMANCE LIQUID CHROMATOGRAPHY

(71) Applicant: DIONEX SOFTRON GMBH, Germering (DE)

(72) Inventors: Daniel Bürger, Raisting (DE); Michael Schadl, Schiltberg (DE)

(73) Assignee: DIONEX SOFTRON GMBH, Germering (DE)

( * ) Notice: Subject to any disclaimer, the term of this patent is extended or adjusted under 35 U.S.C. 154(b) by 600 days.

(21) Appl. No.: 14/080,928

(22) Filed: Nov. 15, 2013

(65) Prior Publication Data
US 2014/0131997 A1    May 15, 2014

(30) Foreign Application Priority Data
Nov. 15, 2012    (DE) .................. 10 2012 110 991

(51) Int. Cl.
G01N 30/60    (2006.01)
(52) U.S. Cl.
CPC .............................. G01N 30/6039 (2013.01)
(58) Field of Classification Search
CPC ... F16L 19/02; F16L 19/0206; F16L 19/0212; F16L 19/025; F16L 19/028;
(Continued)

(56) References Cited

U.S. PATENT DOCUMENTS 2,470,546 A * 5/1949 Carlson .................. F16L 19/12
285/250
2,523,874 A * 9/1950 Moore .................. F16L 33/224
285/250
(Continued)

FOREIGN PATENT DOCUMENTS

CN    86108054 A    6/1987
CN    2087340 U    10/1991
(Continued)

OTHER PUBLICATIONS

BASF Corporation, "Innovations in Laser Welding of Thermoplastics: This Advanced Technology is Ready to be Commercialized," 2002-01-2011, 21 pages, copyright 2003.
(Continued)

*Primary Examiner* — David Bochna
*Assistant Examiner* — James A Linford (57) ABSTRACT

A connector unit for connecting capillaries, for high-performance liquid chromatography includes a connector capillary, a connector housing, and an annular sealing element. The connector capillary projects through a bore of the connector housing. The annular sealing element is provided on a front end region of the connector capillary and which is composed of a plastically and/or elastically deformable material. The connector capillary has an inner shell composed of a plastically and/or elastically deformable material and an outer shell which engages around the inner shell. The inner shell has a radially outwardly extending front end region which, on its own or together with the annular sealing element can generate a seal between the front end region of the connector capillary and a bushing unit.

19 Claims, 3 Drawing Sheets

(58) Field of Classification Search
CPC ............ F16L 19/0286; G01N 30/6039; G01N 30/6034; G01N 30/6026; B01D 15/08; B01D 15/10; B01D 15/14; B01D 15/22; B01L 3/563; B01L 3/5635
USPC .......................................... 422/544, 546, 545
See application file for complete search history.

(56) References Cited

U.S. PATENT DOCUMENTS

| | | | |
|---|---|---|---|
| 2,998,984 A | 9/1961 | Gressel | |
| 3,722,925 A | 3/1973 | Robbins | |
| 3,756,632 A * | 9/1973 | Riggs ...................... | F16L 47/04 |
| | | | 285/250 |
| 3,880,452 A | 4/1975 | Fields | |
| 4,619,473 A | 10/1986 | Someya | |
| 4,968,421 A * | 11/1990 | Spacek ............... | G01N 30/6026 |
| | | | 210/198.2 |
| 5,669,637 A | 9/1997 | Chitty et al. | |
| 5,709,413 A | 1/1998 | Salyers | |
| 6,131,963 A | 10/2000 | Williams et al. | |
| 6,494,500 B1 | 12/2002 | Todosiev et al. | |
| 6,851,729 B2 | 2/2005 | Gibson | |
| 8,006,367 B1 | 8/2011 | Best | |
| 8,037,788 B2 | 10/2011 | Proper | |
| 8,394,275 B2 | 3/2013 | Benevides et al. | |
| 8,569,070 B2 | 10/2013 | Ellis et al. | |
| 8,702,130 B1 | 4/2014 | Zelechonok | |
| 2006/0038402 A1 | 2/2006 | Norman et al. | |
| 2007/0089603 A1 | 4/2007 | Emmons et al. | |
| 2010/0018359 A1 | 1/2010 | Proper | |
| 2010/0156089 A1 | 6/2010 | Zelechonok et al. | |
| 2011/0173786 A1 | 7/2011 | Moshfegh et al. | |
| 2011/0198843 A1 | 8/2011 | Ikenoya et al. | |
| 2011/0278214 A1 | 11/2011 | Benevides et al. | |
| 2011/0298210 A1 | 12/2011 | Hochgraeber et al. | |
| 2012/0024411 A1 | 2/2012 | Hahn et al. | |
| 2012/0061955 A1 | 3/2012 | Hochgraeber et al. | |
| 2012/0223520 A1 | 9/2012 | Graham | |
| 2014/0145437 A1 | 5/2014 | Burger et al. | |

FOREIGN PATENT DOCUMENTS

| | | |
|---|---|---|
| CN | 1389726 A | 1/2003 |
| CN | 101017161 A | 8/2007 |
| DE | 10028503 A1 | 12/2000 |
| DE | 102008059897 | 9/2010 |
| DE | 102009022368 | 11/2010 |
| DE | 102011050037 | 6/2012 |
| EP | 0224188 B1 | 11/1989 |
| EP | 0379401 A1 | 7/1990 |
| GB | 2482175 A | 1/2012 |
| JP | 61191589 U1 | 11/1986 |
| JP | 07167357 | 7/1995 |
| WO | 9936722 A1 | 7/1999 |
| WO | 2009088663 A1 | 7/2009 |
| WO | 2010063267 A1 | 6/2010 |
| WO | 2012010222 A1 | 1/2012 |
| WO | 2012148793 A1 | 11/2012 |
| WO | 2012149930 | 11/2012 |

OTHER PUBLICATIONS

Solvay Specialty Polymers, "Laser Welding Guide: Amodel polyphthalamide (PPA)," Technical Bulletin, 4 pages, copyright 2012.
Chinese Office Action dated Oct. 22, 2014, from Chinese patent application No. 2013105664131.
Search Report dated Oct. 10, 2014, from Chinese patent application No. 2013105664131.

* cited by examiner

CONNECTOR UNIT AND CONNECTING SYSTEM FOR CONNECTING CAPILLARIES, IN PARTICULAR FOR HIGH-PERFORMANCE LIQUID CHROMATOGRAPHY

CROSS REFERENCE TO RELATED APPLICATIONS

This application is claims the priority benefit under 35 U.S.C. § 119 to German Patent Application No. 10 2012 110 991.5, filed on Nov. 15, 2012, the disclosure of which is incorporated herein by reference.

FIELD OF THE INVENTION

The invention relates to a connector unit for connecting capillaries, in particular for high-performance liquid chromatography (HPLC). Furthermore, the invention relates to a fluidic connecting device composed of a bushing unit and of a connector unit.

BACKGROUND

In chromatography systems, liquids or gases are conveyed through suitable connecting lines between the components of the respective system. Said connecting lines which may be composed for example of high-grade steel have, at their ends, suitable connecting systems, also known as fittings, in order to be able to produce a sealed connection to the ports of the components.

A connecting system of said type was described as early as in the year 1975 in U.S. Pat. No. 3,880,452. Here, a capillary which forms the connecting line between two components is inserted into the capillary receiving opening of a bushing unit or a connecting unit and fixed in the bushing by means of a fastening screw which has a central bore for guiding the capillary. For sealing, one or more sealing elements which surround the capillary in the front end region thereof are pressed into the capillary receiving opening, which runs inward in a conical manner, by means of the fastening screw during the connection of capillary and bushing unit.

It is however a disadvantage here that the sealing action is provided not in the plane of the face surface, which is perpendicular to the longitudinal axis of the capillary, but rather is offset rearward from the face surface by a certain distance in an axial direction. This gives rise to a dead volume which has a disadvantageous effect in particular in the field of high-performance liquid chromatography. To be able to ensure the sealing action of such connections at the extremely high pressures used in high-performance liquid chromatography, use is often made of sealing elements such as are described as prior art for example in FIG. 2 of U.S. Pat. No. 4,619,473. These are sealing elements which are of annular cross section and which are normally likewise composed of high-grade steel and which, in longitudinal section, have a partially conical profile of the outer diameter. Here, the capillary projects with its foremost section through the sealing element into a cylindrical recess (pilot bore) in the bushing element. The bushing element widens conically proceeding from the rear end of the pilot bore, wherein the conical widening has a greater angle with respect to the longitudinal axis of the capillary than the sealing element. As a result, as the sealing element is pressed into the receiving opening by means of a fastening screw, an extremely high radially inwardly directed pressure is exerted on the front region of the sealing element, such that the sealing point is formed here. Said pressure however normally results in a deformation of the sealing element and of the capillary, wherein the sealing element is pressed by way of its front edge annularly into the outer circumference of the capillary.

Such a deformation is undesirable in particular because in this way, the sealing element is connected in a positively locking and non-positively locking manner to the capillary, and the sealing element can no longer be readily displaced in an axial direction on the capillary. If the sealing connection is released and if it is sought to screw a connector element of said type in to another bushing unit, for example because a component of the chromatography system must be replaced, then it is duly possible for a sealed connection to be produced again, but owing to tolerances or manufacturer-dependent differences in the depths of the receiving opening, it can no longer be ensured that the capillary, by way of its face surface, acts again on the face surface of the line to be connected. If the receiving opening of the bushing unit of the exchanged component is longer in an axial direction than in the case of the component used previously, an undesired dead volume is formed. If the receiving opening for the capillary in the exchanged component is shorter in an axial direction than in the case of the component used previously, the capillary is even deformed, possibly damaged, under the pressure of the fastening screw, and a sealed connection is no longer possible under some circumstances. This is because the sealing element that is fastened in a positively locking and non-positively locking manner to the capillary cannot move in an axial direction.

However, in the case of such a fitting, a certain dead volume is also scarcely avoidable if the face surfaces of the capillary and of the line to be connected are situated directly opposite or make contact, because the sealing point is situated not in the region of the face surface of the capillary or of the line to be connected.

To solve said problem, DE 10 2009 022 368 discloses a connector unit in which an annular sealing element is provided on the outer side of the capillaries. Said sealing element is inserted together with the capillary into the pilot bore of a bushing housing and has an axial thrust force exerted thereon such that, as a result of plastic or elastic deformation of the sealing element, sealing of the capillary connection is attained already in the region of the base surface of the pilot bore, whereby the formation of a dead volume is prevented. During the disassembly of the connection, the sealing element can also be pulled out of the pilot bore in a relatively simple manner together with the capillary.

Said connector unit is however suitable only for capillaries which, when inserted into the pilot bore, exhibit an adequate amount of space on the outer side of the capillary for the arrangement of the annular sealing element there. Since the above-described form of the bushing element of U.S. Pat. No. 4,619,473 has become established as a standard and, in the field of HPLC, a pilot bore diameter of approximately 1.6 mm has become established as a standard, the suitability of said plug-in connection is restricted to thin capillaries with outer diameters of considerably less than 1.6 mm, for example 200 µm to 500 µm, such as for example fused silica capillaries or else metal capillaries with an outer diameter of for example approximately 0.8 mm. The connector unit is however unsuitable for capillaries with larger outer diameters, such as for example the capillaries with approximately 1.6 mm outer diameter that are widely used in the field of HPLC.

This substantially also applies to the connector unit known from DE 10 2008 059 897 B4 and to the related connecting system for connecting capillaries, in which the front end region of the capillary, which is preferably composed of metal, is flared in a trumpet-like manner. It is achieved in this way that an annular sealing element which surrounds the front end region of the capillary is pressed with an axial pressing force in the direction of the base of a corresponding receiving opening in a bushing unit or of a connecting unit which has a bushing. Here, too, a sealing action is attained in the region of the front face surface of the trumpet-like end region if the diameter of the end region is smaller than the diameter of the receiving opening. As a result of the exertion of load on the rear face side of the annular sealing element by means of the front region, which is displaceable on the capillary, of the connector housing, the sealing element is pushed forward and compressed such that, as a result of a plastic deformation, a sealing action is attained in the annular space formed by the capillary and by the receiving opening (including the base surface thereof) and by the front side of the connector housing. In this way, not only is a very good sealing action attained, but it is also ensured that, when the connection is released, the sealing element is pulled out of the receiving opening together with the capillary, and cannot remain in the receiving opening.

To solve the problem regarding the possibility of using a bushing unit or connecting unit with a pilot bore for receiving a capillary, which pilot bore has an inner diameter that substantially corresponds to the outer diameter of the capillary, it is proposed in DE 10 2011 050 037 B3 that the sealing element be provided within the wall of the front end of the capillary to be connected. Here, the sealing element forms the front end of the capillary. For stabilization of the capillary wall in the region of the sealing element, use is preferably made of a supporting inner pipe.

Furthermore, capillaries are known which, owing to their metal-free, media-contacting inner surface and high pressure resistance, are of multi-part construction. The inner, media-contacting surface is formed by a plastics hose, generally composed of a polyether ether ketone (PEEK). To attain the pressure stability, the plastics hose is embedded into a metallic pipe. To provide the necessary metal-free connections for this purpose, said capillary ends are insert molded with plastic, such that the metal cannot come into contact with the medium at any location.

Already-known connecting systems used on such capillaries of multi-part construction, that is to say on capillaries whose wall is composed of multiple shell layers, have the disadvantage that, in addition to the problems mentioned above, it is also necessary, in the connecting region, to prevent the medium from coming into contact with the metal shell or with a shell layer composed of non-inert material, and to prevent medium from being able to penetrate between the shell layers if the connection between the shell layers of the capillary does not exhibit adequate stability with respect to the pressure of the medium or if the shell layers are not connected to one another at all.

SUMMARY

It is therefore an object of the invention to provide a connector unit for connecting capillaries, which connector unit has an inner shell composed of a plastically deformable material and an outer shell which engages around the inner shell and which is composed of a pressure-resistant material, wherein the connector unit, in conjunction with a suitable bushing unit or connecting unit, ensures a pressure-tight connection as far as possible without a dead volume, and wherein a penetration of the medium between the inner and outer shells is also prevented. Finally, the connector unit should also be easily connectable to a bushing unit or to a connecting unit.

The invention is based on the realization that a capillary which has a relatively soft inner shell composed of a plastically and/or elastically deformable material and an outer shell composed of a hard, pressure-resistant material can, by means of a connector unit, be easily connected in a pressure-tight manner to a bushing unit or to a connecting unit if, in the region of the end at which the connector unit is provided, the inner shell extends beyond the face side of the outer shell and has a front, radially outwardly extending annular end region which, on its own or together with the annular sealing element, and in the connected state of the connector unit and bushing unit, generates a sealing action between the front end region of the connector capillary and the annular face side of the capillary receiving opening of the bushing unit.

In this way, it is achieved that, during the connection of the connector unit to the bushing unit, the radially outwardly extending end region of the inner shell is acted on, at least also between the face side of the outer shell and the base surface of the receiving recess of the bushing unit, with (at least part) of the pressure force with which the connector capillary is pressed into the receiving recess of the bushing unit. Owing to the plastic and/or elastic deformability of the material of the inner shell, the radially outwardly extending end region thus also acts as a sealing element, regardless of whether or not that face surface of the end region which faces toward the bushing unit is still entirely or partially covered by the sealing element.

As a result of the fact that the radially outwardly extending part of the inner shell is acted on with at least a part of the axially acting assembly force, the inner shell is also reliably prevented from collapsing in the region of the connection, that is to say from reducing the cross section of the connector capillary for the medium flowing through the latter. Furthermore, in this way, between the inner and outer shell, there is no formation whatsoever of a gap into which the medium to be conducted could penetrate, even if said medium is at high pressure, such as is the case in HPLC.

It is pointed out at this juncture that, in the present description, the expression "capillary" encompasses both independent capillary-like elements and also capillary-like elements which are fixedly or releasably connected to a further component. These also include, for example, attachment elements of components which are intended for connection to a bushing unit or to a connecting unit.

In one embodiment of the invention, in the connected state of the connector device and bushing unit, the annular space, formed by the circumferential surface of the connector capillary and the inner surface of the capillary receiving opening of the bushing unit, for the sealing element may be delimited at its side facing toward the connector unit by a front face side of the connector housing. In this way, in the case of high axial pressing forces between the connector unit and bushing unit, a situation is prevented in which the material of the sealing element can deflect, by yielding, into a region which is not delimited by an adequately pressure-resistant wall, and in which the sealing pressure within the sealing material regions of the sealing element and of the radially outwardly extending end region of the inner shell is thus reduced. Inward yielding of the material of the inner shell into the cross section that conducts the medium is prevented by the internal pressure of the medium (with suitably selected axial pressing force and/or suitable sealing pressure in the material).

In one embodiment of the connector unit, the connector housing may be of two-part form and have a thrust piece, which exerts load on the sealing element, and an assembly part which, in the connected state of connector unit and bushing unit, exerts an axial pressing force on the thrust piece. As a result of the decoupling of the thrust piece and assembly part, it is achieved that, as the assembly part is screwed into the bushing unit, the thrust piece need not co-rotate. The thrust piece may thus also be connected in an axially fixed manner to the connector capillary.

The radially outwardly extending front end region of the inner shell may be connected in a cohesive and sealing manner to at least one sub-region of the adjoining surface of the sealing element, for example by adhesive bonding, fusion or welding. The connection in a sub-region is preferably configured such that the sub-region extends over the entire circumference. In this way, a situation is prevented in which the medium can penetrate into a region between the sealing element and the front end region of the inner shell, which region is situated, as viewed in the axial direction, beyond the axial position up to which the annular, cohesive connecting region extends.

In one embodiment of the invention, the axially front face surface, that is to say the face surface that faces toward the bushing unit, of the end region at least partially concomitantly forms the front annular face side of the connector capillary or of the connector unit. Here, in the assembled state of the connector unit and bushing unit, the end region has load exerted on it directly by the annular face side of the capillary receiving opening of the bushing unit.

In one embodiment, the end region may extend radially outward to such an extent that its radially outer surface is substantially in alignment with the circumferential surface of the sealing element. This gives rise to the advantage that the end region has the maximum possible radial extent and, in the assembled state of the connector unit and bushing unit, is acted on and securely fixed by the pressing force. Furthermore, the gap through which the liquid medium could penetrate between the inner and outer shells of the capillary is relocated radially further outward. The deformation of the end region and of the sealing element thus yields a further improved sealing action, even if there is no cohesive connection between the end region and the sealing element or between the end region and the face side of the outer shell.

The annular sealing element may also be provided on the axially front face side of the end region and be connected, preferably cohesively, to the end region. In this way, more sealing material is located between the face side of the outer shell and the annular face side of the capillary receiving opening, which sealing material can generate an improved sealing action owing to the greater possible deformation during the assembly process.

A further annular sealing element may also be provided on the axially front face side of the end region in addition to an annular sealing element that extends around the outer shell of the connector capillary, which further annular sealing element is connected, preferably cohesively, to the end region.

In a further embodiment of the invention, the annular sealing element may extend by way of its front face side beyond the front face side of the outer shell of the connector capillary and have an annular, coaxial face-side recess in which the radially outwardly extending front end region of the inner shell is received. This gives rise to an annular contact surface, which runs substantially perpendicular to the longitudinal axis of the connector capillary, between the front, radially running end region of the inner shell and the sealing element, wherein an excellent sealing action is generated owing to the pressure within said materials even if no cohesive connection is provided at said contact surface.

In another embodiment, the annular sealing element may extend by way of its front face side beyond the front face side of the outer shell of the connector capillary, and engage by way of a face-side, radially inwardly directed flange region over the radially outwardly extending end region of the inner shell, such that the end region is fixed in the axial direction by the flange of the sealing element (also even in the non-assembled state of the connector unit and bushing unit). It is thus possible, for example, to prevent the inner shell from being pulled out of the outer shell.

The sealing element and the inner shell of the connector capillary may be composed of the same material, for example of a thermoplastic material, composed in particular of polyether ether ketone (PEEK). The cohesive connection can thus be realized in a simple manner by fusion.

The radially outwardly extending front end region of the inner shell may be produced from a part of the inner shell, which part projects beyond the outer shell and is radially flared and bent radially outward by plastic deformation, preferably by thermal plastic deformation.

In the connecting device according to the invention, the receiving recess of the bushing unit and the connector region of the connector device are formed such that they can be slid axially one inside the other during the connection process, wherein, shortly before the axial end position is reached in which a predefined sealing pressure is attained in the sealing element and in the radially outwardly extending end region of the inner shell, the annular space between the outer circumference of the connector capillary and the inner wall of the capillary receiving recess in the bushing housing is delimited by the front face side of the connector housing. In this way, as already explained above, it is made possible to attain a high sealing pressure within the material of the sealing element and of the front end region of the inner shell, such that the connecting device can be used even in the case of high pressures such as those used in HPLC.

The annular sealing element may have, over its axial extent, a circumferential surface which is parallel to the longitudinal axis of the connector housing and which, in the non-assembled state, is substantially in alignment with the circumferential surface, which is parallel to the longitudinal axis of the connector housing, of that region of the connector housing which exerts load on the sealing element, wherein the outer contour of the cross section in said axial sub-region of the connector device substantially corresponds to the cross section of the outer receiving recess of the bushing unit. This yields the advantage that, during the assembly process, only a relatively small deformation is required during the course of the necessary reduction in volume until the predefined sealing pressure within the material is attained.

BRIEF DESCRIPTION OF THE DRAWINGS

The invention will be explained below on the basis of an exemplary embodiment which is illustrated in more detail in the drawing, in which:

FIG. 7 shows a sixth embodiment which is similar to the variant as per FIG. 6 but in which the annular sealing element which extends around the outer shell of the connector capillary has been dispensed with.

DETAILED DESCRIPTION OF EMBODIMENTS

Figure 1:
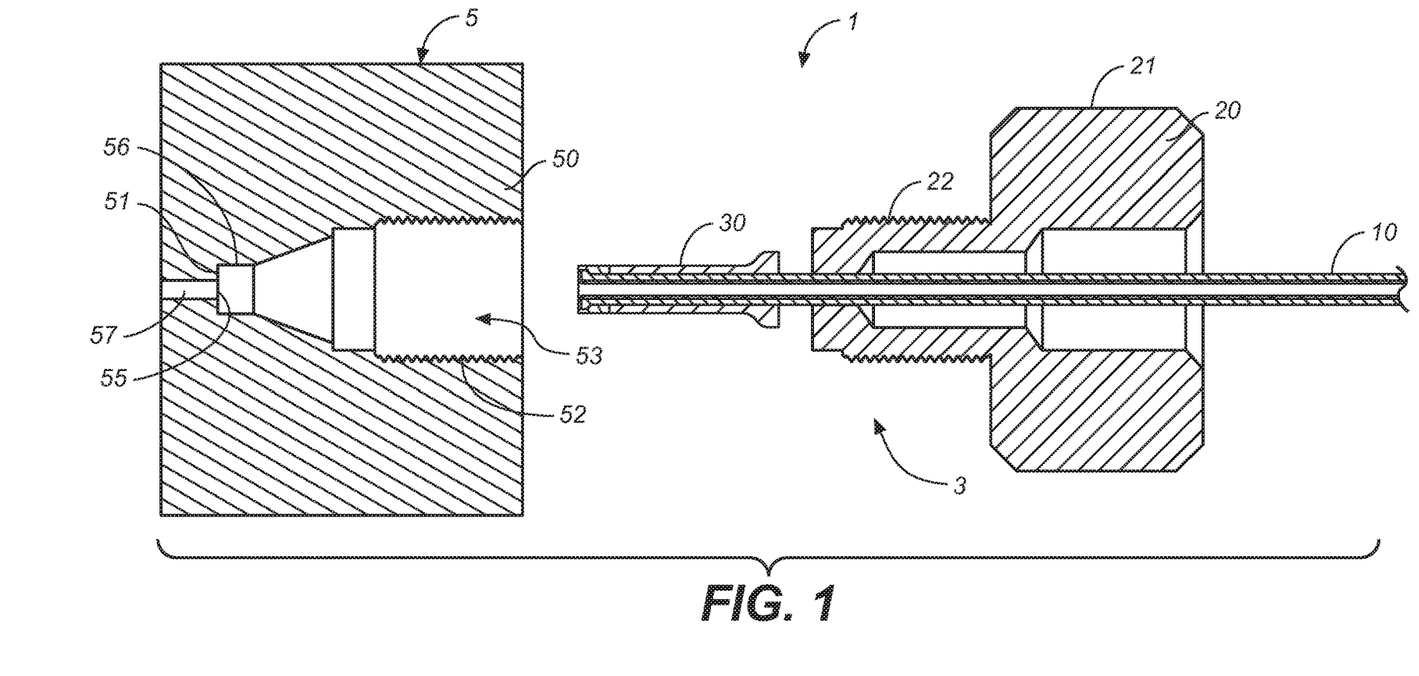
FIG. 1 is a schematic illustration of an embodiment of a connecting device according to the invention having a bushing unit and having a connector unit, in axial longitudinal section and in the non-assembled state.
Figure 2:
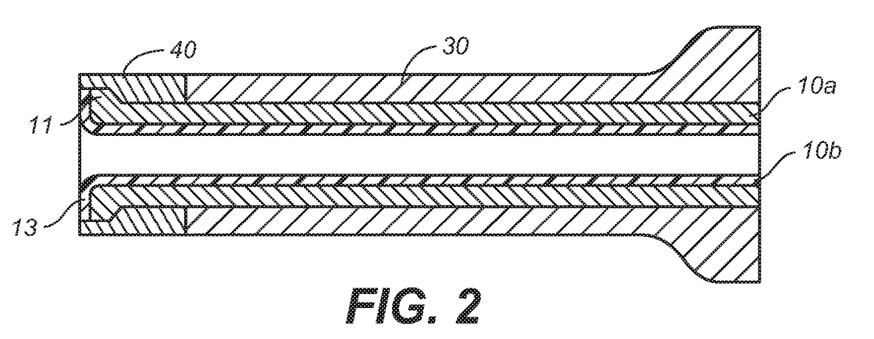
FIG. 2 is an enlarged illustration of the front part of the connector unit in FIG. 1.

The connecting device 1 illustrated in the disassembled state in FIG. 1 comprises a bushing unit 5, which bushing unit is illustrated merely schematically with regard to those outer contours thereof which are not relevant for the invention, and which bushing unit may be arranged for example on a component of a system for high-performance liquid chromatography, for example on a separation column. Furthermore, the connecting system 1 comprises a connector unit 3. The connector unit 3 in turn comprises a connector capillary 10, a connector housing 20 realized in the form of a screw, a thrust piece 30 which may be composed of high-grade steel or of some other metal, and a sealing element 40 which may be composed for example of a material that exhibits adequate elastic and/or plastic deformability, for example a suitable plastic. The connector capillary 10 has an outer shell 10a composed of a pressure-resistant material, for example high-grade steel, and an inner shell 10b composed of a plastic and/or elastic material (FIG. 2). The material of the inner shell 10b may be a thermoplastic material, for example PEEK. In particular, the inner shell 10b and the sealing element 40 may be composed of the same material.

The screw-like connector housing 20 has a thickened head part which is provided with a knurling 21 on the outer circumference and which is adjoined by a threaded part provided with a thread 22. The connector housing 20 has a central bore which, in the exemplary embodiment illustrated, runs in a stepped manner, wherein the inner diameter of the bore in the front region of the threaded part is only slightly larger than the outer diameter of the connector capillary 10 that is received in the central bore. The connector capillary 10 projects by way of its front end through the central bore of the connector housing 20, wherein, in the direction of the end of the connector capillary 10 in front of the connector housing 20, the thrust piece 30 is arranged radially around the connector capillary 10.

The bushing unit 5 has a merely schematically illustrated bushing housing 50 in which there is provided a receiving recess 53 for receiving the connector unit 3. The receiving recess is composed of a first region which is of relatively large diameter and in which there is also provided an internal thread 52, such that the threaded part of the connector unit can be screwed therein. The first region of the receiving recess is adjoined by a conical region which tapers to the diameter of a capillary receiving opening or pilot bore 56, said diameter corresponding to the outer diameter of the thrust piece 30.

The opening cross section 55 of a bore 57, whose diameter in the exemplary embodiment illustrated corresponds to the inner diameter of the connector capillary, opens out into the base surface 51 of the pilot bore 56. Instead of the bore 57 and the opening cross section 55 thereof, it is also possible for a bushing capillary (not illustrated) to be held in the bushing unit 5, the opening cross section of which bushing capillary then corresponds to the opening cross section 55 of the bore 57. For this purpose, instead of the bore 57, there may be provided a bore of larger diameter in which the front end of a bushing capillary is held, for example by adhesive bonding. This ultimately likewise yields the structure, schematically illustrated in FIG. 1, of a bushing unit.

The outer diameter of the rotationally symmetrical thrust piece 30 in the rear region thereof may also correspond to the inner diameter of the first region of the receiving recess 53 of the bushing unit 5, in order to ensure guidance of the thrust piece or of the front end of the connector capillary during the assembly of the connector unit and bushing unit. The outer diameter of the front region of the thrust piece 30 corresponds to the inner diameter of the pilot bore 56.

As can be seen from the enlarged illustration, shown in FIG. 2, of the front region of the connector unit in FIG. 1, the annular sealing element 40 is arranged on the end of the connector capillary 10. The end of the outer shell 10a of the connector capillary 10 has a load exertion region 11 of larger outer diameter, which load exertion region may be realized as a thickened end region with an encircling shoulder. Instead of a thickened portion, it is also possible for the front end region of the outer shell to be widened in a trumpet-like manner (with a uniform or tapering wall thickness).

The maximum outer diameter of the front region 11 is smaller than the inner diameter of the pilot bore 56 that is delimited by the base wall 51. The outer diameter of the sealing element 40 corresponds substantially to the inner diameter of said cylindrical inner region of the receiving opening 53.

In its front region facing toward the load exertion region 11, the inner diameter of the sealing element 40 is formed in a substantially complementary manner with respect to the contour of the outer diameter of the load exertion region 11, such that the sealing element 40 can be pushed without a high pressure, and without a high axially acting force, onto the load exertion region 11. Here, the sealing element may project beyond the face side of the load exertion region 11 already in the non-assembled state of the bushing unit 5 and connector unit 3. The contour of the inner diameter in the front region of the sealing element 40 may however also be formed such that said sealing element can be pushed onto the load exertion region 11 without pressure only as far as an axial position in which the face surface of the sealing element 40 is still set back by a certain distance in relation to the face surface of the load exertion region 11 or of the connector capillary 10.

As can be seen from FIG. 2, the inner shell 10b of the connector capillary has a radially outwardly extending end region 13 which extends around over the face side of the load exertion region 11 and which may also bear against or be connected to said load exertion region already in the non-assembled state. It is not necessary here for the end region 13 to extend in the radial direction as far as the outer diameter of the load exertion region 11 or of the front face side of the outer shell 10a. In this case, the sealing element may have a region which projects radially inward in front of the face side of the outer shell 10a and which extends preferably as far as the end region 13.

The sealing element may also be connected to the front end region of the outer shell and to the load exertion region (at the circumferential surface thereof and if appropriate at the face side thereof), for example by adhesive bonding or insert molding of the outer shell with a material that forms the sealing element.

The radially outwardly extending end region 13 may also be connected at its contact surface to the sealing element 40. This may likewise be realized by adhesive bonding or welding.

The materials of the end region 13 or inner shell 10b and of the sealing element 40 may also be identical. As material, use is made, for example, of an inert plastics material, for example PEEK. The connection can then be realized in a simple manner by fusion.

For the assembly of the connector unit 3, firstly the connector housing 20, the thrust piece 30 and the sealing element 40 are pushed onto the connector capillary 10 from the front, the outer shell 10a of which connector capillary does not yet have a radially thickened load exertion region 11 in this state. Subsequently, it is then possible for the load exertion region 11 of the outer shell 10a to be produced by means of a suitable tool, for example by upsetting or the like.

If possible, it may self-evidently also be provided that the load exertion region 11 of the connector capillary 10 has already been produced and, in this case, the other components of the connector unit 3 are pushed onto the connector capillary 10 from the respective other end thereof.

The sealing element 40 may also be in the form of a ring element which is slotted in an axial direction, such that the sealing element 40 can then be pushed onto the connector capillary 10 from the front, over the thickened load exertion region 11, or plugged onto the connector capillary 10 from the side. For this purpose, the material of the sealing element 40 must self-evidently exhibit an adequate degree of elasticity.

The radially outwardly extending end region of the inner shell 10b may be produced, for example by thermal deformation, from a part of the inner shell 10b which projects beyond the outer shell 10a. Here, a connection between the face side of the load exertion region 11 and the end region 13 may also be produced at the same time. If desired, it is then also possible for a connection to be produced between the end region 13 and the sealing element 40 in the encircling contact surface, for example by welding or adhesive bonding.

After the components 20, 30 and 40 have been pushed onto the connector capillary 10 and the load exertion region 11 and the end region 13 have been produced and, if appropriate, the materials of said regions have been connected, the connector unit 3 can then be inserted into the bushing unit 5.

The insertion takes place in a simple manner by virtue of the connector housing 20 being pushed forward onto the capillary 10 in the direction of the load exertion region 11 without force until, as a result, the thrust piece 30 (and if appropriate the sealing element 40) is/are moved into an unpressurized forward position. Subsequently, or at the same time, the connector unit 3 is inserted into the receiving opening 53 of the bushing unit 5, and the thread 22 of the threaded part of the connector unit 3 is screwed into the internal thread 52 of the receiving opening 53. During the screwing-in process, the front face surface of the connector housing 20 exerts an axial force via the thrust piece 30 on the sealing element 40, which in turn exerts the axial force on the connector capillary 10 via the load exertion region 11. In this way, the connector capillary 10 is pressed in an abutting manner by way of its face surface against the base wall 51 of the pilot bore 56, wherein centering of the connector capillary 10 in the pilot bore is ensured by means of the sealing element 40 and the front region of the thrust piece 30. As a result of the further screwing-in of the connector housing 20 into the bushing housing 50 of the bushing unit 5, the axial force exerted on the sealing element 40 and on the end region 13 of the inner shell 10b via the displaceable thrust piece 30 is increased. The sealing element, during the elastic and/or plastic deformation thereof, transmits corresponding pressure forces to the load exertion region 11 and thus to the end region 13. At the same time, the pressure prevailing in the material of the sealing element 40 is also exerted on the inner circumferential surface of the pilot bore 56. The sealing element 40 and the end region 13 are thus situated in a practically closed annular space, the walls of which are acted on by the pressure in the materials of the sealing element 40 and of the end region 13. Said sealing pressure is preferably selected to be higher than the pressure of the medium to be conducted, such that the connection between the bushing unit and connector unit exhibits the desired sealing action. Here, only low forces are required for the screwing-in of the connector housing 20 into the bushing housing 50 in order to generate high pressure forces within the sealing element 40 and the end region 13.

From the illustration of FIGS. 1 and 2, it is immediately clear that, for different outer diameters of connector capillaries 10, it is necessary merely to use thrust pieces 30 and sealing elements 40 that are correspondingly adapted in terms of their inner diameter, whereas the connector housing 20 can remain unchanged, assuming that the central bore in the front region of the threaded part 22 is large enough to receive the respective connector capillary 10.

Different depths of receiving openings 53, which may vary for tolerance-related or manufacturer-related reasons, can likewise be compensated by virtue of the threaded part of the connector housing 22 having an adequate length in the axial direction.

The design of a connector unit 3 illustrated in the drawing ensures, even in the case of different depths of the pilot bore 56 of the bushing unit 5, that the face surface of the connector capillary 10 (that is to say the face-side annular surface of the end region 13) is always pressed with a defined force against the base wall 51 of the pilot bore 56.

It is pointed out at this juncture that the thrust piece 30 need not imperatively be displaceable on the connector capillary 10, because the sealing element 40, or at least the end region 13, fills the annular space to be sealed, including the space in front of the face surface of the outer shell 10a. If the tolerances are selected such that the outer circumference of the sealing element substantially corresponds to the diameter of the pilot bore and the compression of the material in front of the face surface of the outer shell 10a is sufficient to generate the required pressure or sealing forces, the thrust piece may also be fixedly connected to the outer shell 10a of the connector capillary 10. This may be realized, for example, by crimping.

For the disassembly of the connecting device 1, it is necessary merely for the connector housing 20 to be unscrewed from the bushing housing 50 and for the connector capillary 10 to be pulled, together with the thrust piece 30 and the sealing element 40, out of the receiving opening 53. Here, the diameter enlargement in the region of the load exertion region 11 of the connector capillary 10 ensures that, when the connector capillary 10 is pulled out, the sealing element 40 does not remain in the pilot bore 56 and have to be removed subsequently with great effort. If the connector unit 3 is to subsequently be mounted again, if appropriate in another (similar) bushing unit 5, the sealing element 40 may if appropriate also be exchanged.

If it is not possible, as described above, for a new sealing element to be pushed onto the capillary over the load exertion region 11 (or for the connector unit 3 to be pushed on from the other end of the connector capillary 10), it is possible, if appropriate, for the foremost end of the connector capillary 10 with the load exertion region 11 to be cut off, and for a new load exertion region 11 to be produced after the required components of the connector unit 3, in particular a new sealing element 40, have been pushed on again.

As already mentioned, as material for the sealing element 40 and for the inner shell 10b, use may be made of for example PEEK or a material with suitable chemical and physical properties.

Figure 3:
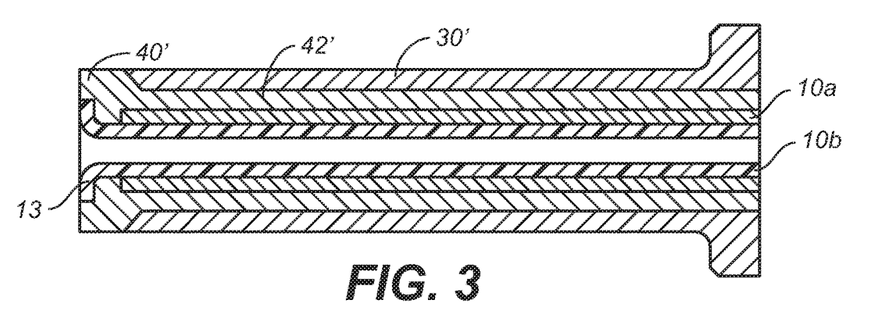
FIG. 3 is a schematic illustration of the front part of a second embodiment of a connector unit according to the invention, having a sealing element crimped onto the capillary.

FIG. 3 shows a further embodiment of a front region of a connector unit as illustrated in FIG. 1, wherein the provision of a load exertion region of the outer shell 10a with enlarged outer diameter has however been omitted. In this variant, the fixing of the sealing element 40' is realized by means of a thrust piece 30 which extends around the sealing element 40 by way of a relatively thin wall in a rear region 42. The fixing of the sealing element 40 on the connector capillary 10 or the outer shell 10a of the connector capillary 10 may preferably be realized by frictional engagement. For this purpose, it is possible for the thrust piece 30' to be deformed, preferably over an axially extended region, by crimping, such that an axially fixed connection is produced between the thrust piece 30, the sealing element 40 and the connector capillary 10 or the outer shell 10a of the connector capillary 10.

In the variant illustrated in FIG. 3, the front region of the sealing element 40' is formed such that the outer diameter substantially corresponds to the outer diameter of the thrust piece 30'. Said outer diameter corresponds to the inner diameter of the pilot bore 56, such that a centering action is generated already during the insertion of the front end of the connector capillary 10 with the sealing element 40' and the thrust piece 30'. The front end of the sealing element 40' is furthermore formed such that an annular shoulder extends from the front face side of the outer shell 10a substantially as far as the outer diameter of the inner shell 10b. At its face side, the sealing element 40' has an annular depression into which, in turn, the radially outwardly extending end region 13 of the inner shell 10b extends. The outer end region 13 is received in said annular space such that the front face surface of the end region 13 is in alignment with the front face surface of the sealing element 40'.

For high-pressure applications in particular, the contact surfaces between the sealing element 40' and the radially outwardly extending end region 13 may again be connected to one another, for example by adhesive bonding, welding or fusion.

In the embodiment illustrated in FIG. 3, the sealing element 40' is provided such that a considerably larger material region is situated in front of the face surface of the outer shell 10a. In this way, an adequate sealing action is attained in all situations, even if the thrust piece 30' is fixedly connected to the connector capillary 10. Owing to the adequate amount of plastically and/or elastically deformable material of the sealing element 40' and of the end region 13, said amount of material can in all situations be deformed to such an extent that the space between the inner wall of the pilot bore and the face surface of the outer shell 10a, or that face surface of the thrust piece 30' which exerts load on the sealing element 40', is completely filled, and that furthermore, in said sealing space, a pressure sufficient for ensuring the desired sealing action is generated within the material.

Figure 4:
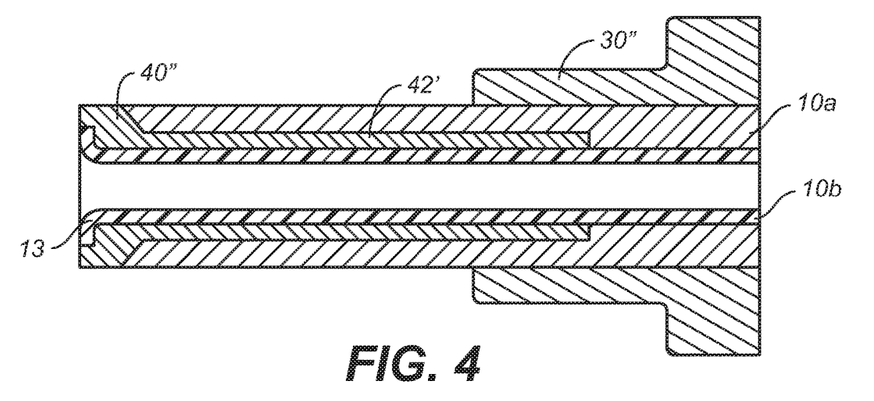
FIG. 4 is a schematic illustration of the front part of a third embodiment of a connector unit according to the invention, having a sealing element arranged between the shell layers of the capillary.

The variant illustrated in FIG. 4 differs from the embodiment as per FIG. 3 substantially in that the sealing element 40" engages by way of its rear region 42" into an annular space between the outer shell 10a and the inner shell 10b. Here, the outer shell 10a, by way of its front face side, performs the task of the thrust piece in FIG. 3 by exerting load on the rear face side of the sealing element 40". The axial force for the pushing-in or pressing-in of the front region of the connector capillary 10, including the sealing element 40", is in this case transmitted via a thrust piece 30" fixed axially on the connector capillary 10. The thrust piece 30" may in turn be mounted in an axially fixed manner on the connector capillary 10 or on the outer shell 10a by crimping. The crimping takes place preferably in a region in which a front region of the thrust piece 10 still extends around the rear region 42" of the sealing element over an adequate axial length. Furthermore, the crimping preferably takes place over an axially extended region in order to ensure adequate fixing of the thrust piece 30" without the need for excessive deformation in the radial direction. Since both the rear region 42" of the sealing element 40" and also the inner shell 10b are composed of a relatively easily deformable material, it may possibly be the case—depending on the dimensioning of said parts and depending on the material properties—that the crimping of the thrust piece 30" does not provide axial fixing of the sealing element 40" sufficient to prevent the sealing element 40" from remaining in the pilot bore 56 during the disassembly of the connecting device. In this case, the sealing element 40" may be connected cohesively to the outer shell 10a and/or to the inner shell 10b.

The outer diameter of the sealing element 40" in the front region corresponds to the outer diameter of the outer shell 10a of the connector capillary 10. The radially outwardly extending end region 13 of the inner shell 10b is formed in the same way as illustrated in FIG. 3. The same applies to the structure of the sealing element 40" in the region in front of the front face side of the outer shell 10a. Here, too, an annular space of the sealing element 40" is provided for the engagement of the end region 13. In the embodiment illustrated in FIG. 4, the generation of an axial pressing force during the insertion of the connector unit 3 into the pilot bore 56 of the bushing unit 5 is ensured by means of a thrust piece 30" which is axially fixedly connected to the connector capillary 10 or to the outer shell 10a thereof. This again may be performed by means of crimping.

To produce the embodiment as per FIG. 4, the outer shell 10a of the connector capillary 10 may be drilled out over the required axial length before the insertion of the inner shell 10b composed of deformable material. The sealing element 40" may subsequently be inserted into the drilled-out region. In a subsequent step, the inner shell 10b may be inserted. The deformation of the shell 10b in the front region in order to produce the radially outwardly extending end region 13 may take place as described above. The same applies to the possibly desired connection of the end region 13 to the sealing element 40″ in at least a part of the contact surfaces.

This variant offers the advantage that the outer diameter of the connector capillary 10 can be selected to be of such a size as to correspond to the inner diameter of the pilot bore 56.

All of the variants illustrated in FIGS. 1 to 4 have in common the fact that a radially outwardly extending end region of the inner shell 10b of the connector capillary 10 is provided, which end region is acted on with an axial pressing force between the base wall 51 of the pilot bore 56 and the face side of the outer shell 10a or the front face side of the thrust piece 30, 30′, such that said region of the inner shell 10b is fixed in the bushing unit. In this way, the shell, composed of deformable material, in the connecting device is reliably prevented from collapsing. Furthermore, said region contributes to generating the desired sealing action. Despite the formation of the connector capillary with at least one inner shell and one outer shell, it is reliably ensured that the medium to be conducted cannot penetrate into a gap that may be present between the shells.

Figure 5:
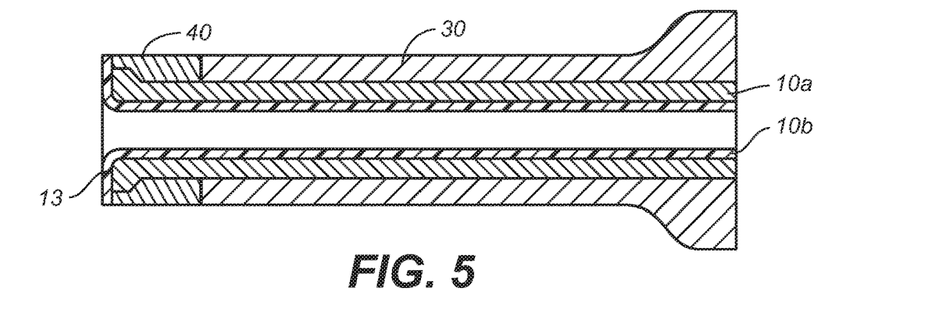
FIG. 5 is a schematic illustration of the front part of a fourth embodiment of a connector unit according to the invention, in which the radially extending end region of the inner shell has a maximum radial extent.
Figure 6:
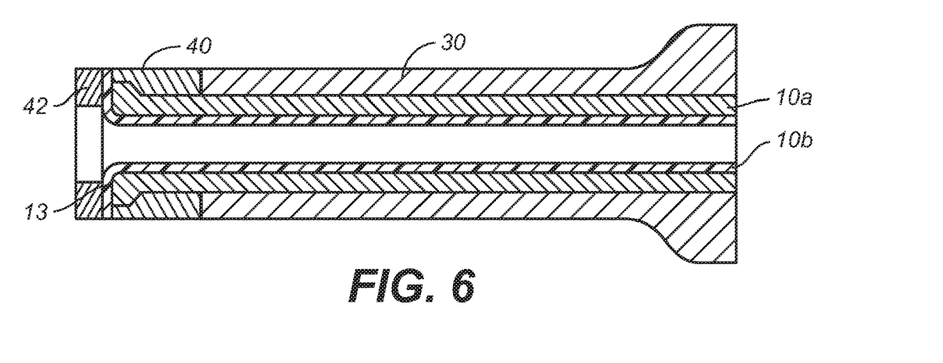
FIG. 6 shows a fifth embodiment which corresponds substantially to the variant as per FIG. 5, but in which a further annular sealing element is connected to the face side of the radial end region.

FIGS. 5 to 8 show further variants for a suitable design of the front region of the connector capillary 10. The variants as per FIGS. 5 and 6 are similar to the variant as per FIG. 2, such that the same reference signs are used here. By contrast to the variant as per FIG. 2, it is however the case in these variants that the end region 13 extends outward in the radial direction to such an extent that the radial outer surface is substantially in alignment with the circumferential surface of the sealing element 40. This has the result, in the assembled state of the connector unit 3, that the end region 13 is securely fixed between the face side of the outer shell 10a and the base of the pilot bore 56 of the receiving recess 53.

In the variant as per FIG. 6, in addition to the annular sealing element 40, a further annular sealing element 42 is provided on the face side of the connector capillary 10 or on the front face side of the end region 13. The sealing element 42 is connected, preferably cohesively, to the end region 13 in order to prevent the sealing element 42 from remaining in the receiving recess 53 during the disassembly of the bushing unit 5 and connector unit 3. The sealing element 42 introduces additional sealing material into the pilot bore 56, such that even in the case of relatively large tolerances, there is an adequate amount of deformable sealing material available to ensure the sealing action of the connection.

Figure 7:
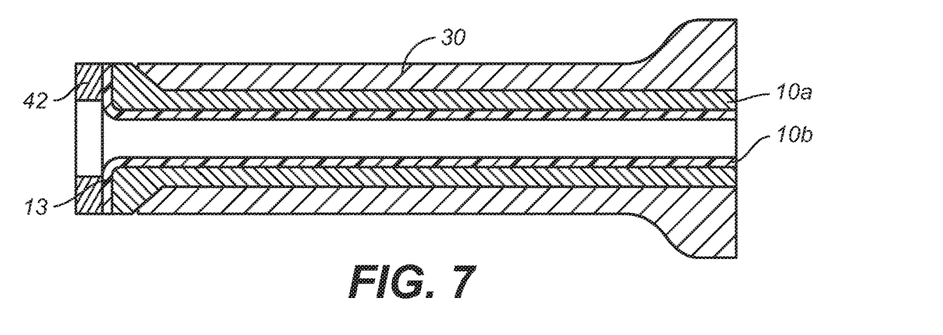

In the variant as per FIG. 7, by contrast to the variant as per FIG. 6, the sealing element 40 has been dispensed with. Here, the thrust piece 30 can exert load on the front, thickened region of the outer shell 10a on the rear side thereof in order to generate the pressing force between the bushing unit 5 and the connector unit 3. Here, the thrust piece may be provided on the connector capillary 10 in a displaceable or else axially fixed manner.

Figure 8:
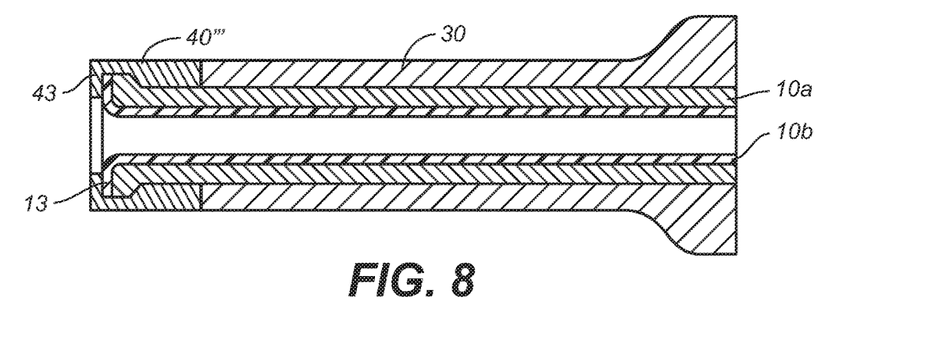
FIG. 8 shows a seventh embodiment having an annular sealing element which engages, by way of a radially inwardly extending flange region, over the radially extending end region of the inner shell.

The variant as per FIG. 8 is likewise similar to the variant as per FIG. 2, wherein here, the sealing element 40‴ has a front, radially inwardly extending flange region 43 which engages over the end region 13. In this way, a situation is prevented in which the inner shell 10b is pulled out of the outer shell 10a when a corresponding axial force acts on the inner shell. In the example illustrated, the radial end region 13 extends as far as the circumferential surface of the front, thickened region of the outer shell 10a. This is however not imperatively necessary. The sealing element may also engage over the thickened region at the front face side thereof.

In the embodiment of FIG. 8, the sealing element 40‴ may be of elastic form, or designed with regard to its structure, such that it can be clipped onto the front region of the connector capillary 10. The sealing element 40‴ may however also be manufactured by insert molding of the front region of the connector capillary after the production of the end region 13. In the variant as per FIG. 8, it is again possible for a cohesive connection to be provided between the sealing element 40′ and the end region 13. Here, the thrust piece 30 may likewise be arranged on the connector capillary 10 in an axially fixed or else displaceable manner.

LIST OF REFERENCE SIGNS

1 Connecting device
3 Connector unit
5 Bushing unit
10 Connector capillary
10a Outer shell
10b Inner shell
11 Load exertion region
13 End region of the inner shell 10b
20 Connector housing
21 Knurling
22 Thread
30, 30′, 30″ Thrust piece
40, 40′, 40″ Sealing element
42 Further sealing element
50 Bushing housing
51 Base wall
52 Internal thread
53 Receiving recess
55 Opening cross section
56 Pilot bore/capillary receiving opening
57 Bore

What is claimed is:

1. A connector unit to connect capillaries comprising:
   (a) a connector capillary;
   (b) a connector housing in which the connector capillary projects through a bore of the connector housing;
   (c) an annular sealing element that is on a front end region of the connector capillary, the annular sealing element including a deformable material;
   (d) in which the connector housing is formed to be releasably connectable to a bushing unit;
   (e) a thrust piece arranged radially around the connector capillary, the thrust piece is configured to exert a load on the annular sealing element, and the connector housing is configured to exert an axial pressing force on the thrust piece;
   (f) in which, in a connected state of the connector unit and the bushing unit,
      (A) the front end region of the connector capillary is configured to project by way of the annular sealing element into a capillary receiving opening of the bushing unit, wherein a face-side opening cross section of the connector capillary is situated opposite, and in alignment with, an opening cross section of the bushing unit, and
      (B) the connector capillary is configured to be pressed by way of the annular sealing element into the capillary receiving opening of the bushing unit with the axial pressing force generated by the connector housing via the thrust piece such that a sealing action is generated between the front end region of the connector capillary and the capillary receiving opening of the bushing unit, (g) in that the connector capillary has an inner shell including a deformable material and an outer shell which engages around the inner shell and extends entirely through the thrust piece, and where the outer shell is composed of a pressure-resistant material, (h) in that the inner shell has a radially outwardly extending front end region which, in the connected state of the connector unit and the bushing unit, generates a sealing action between the front end region of the connector capillary and an annular face side of the capillary receiving opening of the bushing unit, and (i) in which the radially outwardly extending front end region is a portion of the inner shell that axially projects beyond the outer shell and is radially flared and bent radially outward, wherein the annular sealing element extends entirely through the thrust piece, has an outer diameter equivalent to an outer diameter of the thrust piece, and which can abut the capillary receiving opening of the bushing unit.

2. The connector unit according to claim 1, in that the radially outwardly extending front end region of the inner shell is connected in a cohesive and sealing manner to at least one annularly closed sub-region of an adjoining surface of the annular sealing element.

3. The connector unit according to claim 2, in that the radially outwardly extending front end region of the inner shell has a cohesive connection to the adjoining surface of the annular sealing element where the cohesive connection is selected from the group consisting of an adhesive bonding, a fusion, and a welding.

4. The connector unit according to claim 1, in that a front face surface of the front end region of the connector capillary at least partially concomitantly forms a front annular face side of the connector capillary.

5. The connector unit according to claim 1, in that the front end region extends radially outward so that a radial outer surface of the connector capillary is in alignment with a circumferential surface of the annular sealing element.

6. The connector unit according to claim 5, in which the circumferential surface is parallel to a longitudinal axis of the connector housing.

7. The connector unit according to claim 1, in that the annular sealing element is on an axially front face side of the front end region, and in that the annular sealing element is connected to the front end region.

8. The connector unit according to claim 1, in that a front face side of the annular sealing element extends beyond a front face side of the outer shell of the connector capillary and the annular sealing element includes an annular, coaxial face-side recess in which the radially outwardly extending front end region of the inner shell is received.

9. The connector unit according to claim 1, in that a front face side of the annular sealing element extends beyond a front face side of the outer shell of the connector capillary, and where a face side of a radially inwardly directed flange region engages over the radially outwardly extending front end region of the inner shell.

10. The connector unit according to claim 1, in that the annular sealing element and the inner shell of the connector capillary are composed of a same material.

11. The connector unit according to claim 10, in that the same material comprises a polyether ether ketone (PEEK).

12. The connector unit according to claim 1, in that the inner shell has the radially outwardly extending front end region together with the annular sealing element, in the connected state of the connector unit and the bushing unit, generate the sealing action between the front end region of the connector capillary and the annular face side of the capillary receiving opening of the bushing unit.

13. The connector unit according to claim 1, in that the sealing action includes an elastic deformation of the annular sealing element.

14. The connector unit according to claim 1, in that the sealing action includes a plastic deformation of the annular sealing element.

15. The connector unit according to claim 1, in that the inner shell includes a plastic and the outer shell includes a metal.

16. A connecting device to fluidically connect capillaries comprising:

(a) a connector unit including a connector capillary, a connector housing, and an annular sealing element;

(b) in which the connector capillary projects through a bore of the connector housing;

(c) in which the annular sealing element is on a front end region of the connector capillary, the annular sealing element including a deformable material;

(d) a thrust piece arranged radially around the connector capillary, the thrust piece is configured to exert a load on the annular sealing element, and the connector housing is configured to exert an axial pressing force on the thrust piece;

(e) a bushing unit including a bushing housing, in which the connector housing is formed to be releasably connectable to the bushing housing, wherein the bushing housing has a capillary receiving opening, at a base surface of which an opening cross section of a fluid line that is formed in the bushing housing, issues into an interior of the capillary receiving opening;

(f) in which, in a connected state of the connector unit and the bushing unit, (A) the front end region of the connector capillary projects by way of the annular sealing element into the capillary receiving opening of the bushing unit, wherein a face-side opening cross section of the connector capillary is situated opposite, and in alignment with, an opening cross section of the bushing unit, and (B) the connector capillary is pressed by way of the annular sealing element into the capillary receiving opening of the bushing unit with the axial pressing force generated by the connector housing via the thrust piece such that a sealing action is generated between the front end region of the connector capillary and the capillary receiving opening of the bushing unit, (g) in that the connector capillary has an inner shell including a deformable material and an outer shell which engages around the inner shell and extends entirely through the thrust piece, and where the outer shell includes a pressure-resistant material, and (h) in that the inner shell has a radially outwardly extending front end region which, in the connected state of the connector unit and the bushing unit, generates a sealing action between the front end region of the connector capillary and an annular face side of the capillary receiving opening of the bushing unit, in which the radially outwardly extending front end region is a portion of the inner shell that axially projects beyond the outer shell and is radially flared and bent radially outward, wherein the annular sealing element extends entirely through the thrust piece, has an outer diameter equivalent to an outer diameter of the thrust piece, and which can abut the capillary receiving opening of the bushing unit.

17. The connecting device according to claim 16, in that a connector region of the connector unit is slidable axially into a receiving recess of the bushing unit so that the annular sealing element is at a predefined sealing pressure, and in the radially outwardly extending front end region of the inner shell.

18. The connecting device according to claim 17, in that the annular sealing element has a circumferential surface which is parallel to a longitudinal axis of the connector housing and which, in a non-assembled state, is in alignment with the circumferential surface, which is parallel to the longitudinal axis of the connector housing, of that region of the connector housing which exerts a load on the annular sealing element, wherein an outer contour of a cross section in an axial sub-region of the connector unit corresponds to a cross section of an outer receiving recess of the bushing unit.

19. The connecting device according to claim 16, in that the inner shell includes a plastic and the outer shell includes a metal.

\* \* \* \* \*